US008648034B2

(12) United States Patent
Chang et al.

(10) Patent No.: US 8,648,034 B2
(45) Date of Patent: Feb. 11, 2014

(54) METHOD AND APPLICATIONS OF PEPTIDE-MEDIATED MITOCHONDRIAL DELIVERY SYSTEM

(75) Inventors: Jui-Chih Chang, Chcanghua County (TW); Chin-San Liu, Changhua County (TW)

(73) Assignee: Changhua Christian Hospital, Changhua County (TW)

( * ) Notice: Subject to any disclaimer, the term of this patent is extended or adjusted under 35 U.S.C. 154(b) by 9 days.

(21) Appl. No.: 13/315,432

(22) Filed: Dec. 9, 2011

(65) Prior Publication Data

US 2013/0149778 A1    Jun. 13, 2013

(51) Int. Cl.
*A61K 38/00*    (2006.01)
*A61K 47/00*    (2006.01)

(52) U.S. Cl.
USPC ................................................. 514/1.2

(58) Field of Classification Search
None
See application file for complete search history.

(56) References Cited

PUBLICATIONS

Jordan et al "Optimizing Electroporation Conditions in Primary and Other Difficult-to-Transfect Cells" J Biomolecular Techniques 19:328-334. Published Dec. 2008.*
ATCC "All collection Search" Accessed on the Internet Jan. 15, 2013. <http://www.atcc.org/ATCCAdvancedCatalogSearch/AllCollectionSearch/tabid/454/Default.aspx>.*

Chang et al "Peptide-mediated mitochondrial transfer can rescue mitochondrial respiratory functions in cybrids harboring MERRF A8344G mutation" The 7th Conference of Asian Society for Mitochondrial Research and Medicine and 10th Conference of Japanese Society of Mitochondrial Research and Medicine. Dec. 16, 2010.*
Chang et al "Functional Recovery of Human Cells Harbouring the Mitochondrial DNA Mutation MERRF A8344G via Peptide-Mediated Mitochondrial Delivery" Neuro-Signals 21:160-173. Published online Sep. 21, 2012.*
Jui-Chih Chang et al., Peptide-mediated mitochondrial transfer can rescue mitochondrial respiratory functions in cybrids harboring MERRF A8344G mutation, Mitochondria, Life and Intervention, The 7th Conference of Asian Society for Mitochondrial Research and Medicine (ASMRM) and 10th Conference of Japanese Society of Mitchondrial Research and Medicine (J-mit), Dec. 2010, pp. 116.

* cited by examiner

*Primary Examiner* — Cecilia J Tsang
*Assistant Examiner* — Zachary J Miknis
(74) *Attorney, Agent, or Firm* — WPAT, P.C.; Anthony King (57) ABSTRACT

The present invention relates to a method using a cell penetrating peptide (Pep-1) for labeling and delivering mitochondria separated from healthy cells to replace damaged mitochondria. At present, microinjection of mitochondria into cells can only process one cell at a time, and therefore, this technique is limited to embryo related research and relevant applications. The advantages of the said peptide-mediated mitochondrial delivery system (PMD) include less steps with more efficiency, where a number of cells can be treated following one labeling process; the delivery process can be easily controlled, there is no cell toxicity after delivery under appropriate conditions, and delivery efficiency is over 80% depending on different cell types. Mitochondria delivered by the PMD system will move to the original mitochondrial location in the cells and will not be catalyzed in lysosomes; thus, the therapeutic effects can last at least one week.

15 Claims, 11 Drawing Sheets
(4 of 11 Drawing Sheet(s) Filed in Color)

SEQUENCE LISTING

```
<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: Penetrating Peptide (Pep-1) for Labelling and
      Delivering Mitochondria
<220> FEATURE:
<221> NAME/KEY: SITE
<222> LOCATION: (22)...(22)
<223> OTHER INFORMATION: Cys is decarboxylated

<400> SEQUENCE: 1

Lys Glu Thr Trp Trp Glu Thr Trp Trp Thr Glu Trp Ser Gln Pro
1               5                   10                  15

Lys Lys Lys Arg Lys Val Cys
            20
```

METHOD AND APPLICATIONS OF PEPTIDE-MEDIATED MITOCHONDRIAL DELIVERY SYSTEM

BACKGROUND OF THE INVENTION

1. Field of the Invention

The present invention relates to a method using a cell penetrating peptide (Pep-1) for labeling and delivering mitochondria separated from normal cells to replace dysfunctional mitochondria in deficient cells.

2. Description of the Prior Art

The necessity and demand for mitochondria transplantation is high because mitochondrial defects are involved in many diseases with unknown reasons and no cure is currently available. Majority of the DNA mutations found in organelles (mitochondria) in cytoplasm are inherited genetic diseases; yet, some are caused by gene mutations. The defects are usually passed from mothers to their children because each egg has thousands of mitochondria, and upon fertilization, the mitochondria of sperms were left outside of the zygote; hence, the mitochondrial DNA in the zygote all came from the mother. The incidence of mitochondrial defects and the distribution of these rare diseases caused by mitochondrial DNA, are random since each cell contains thousands of mitochondria, and each mitochondria has 2~10 mitochondrial DNA; which mitochondrial DNA has defects is uncertain. In Taiwan, around 50 mitochondrial defects—related diseases were reported up to date, and these diseases are categorized as rare diseases; furthermore, roughly 300~400 domestic families in Taiwan are found to have mitochondrial DNA defects with a defect rate around 1/10,000.

Mitochondrial defects are widely involved in numerous diseases and malignancies with ever-changing clinical symptoms. For the age of the onset of the diseases, from newborn babies to adults, some symptoms are persistent and apparent (e.g. developmental retardation and seizure, etc); On the other hand, some are non-specific symptoms such as migraine and short stature, etc., and only become apparent when in poor physical conditions. Different organs may have various degrees of lesions, for instance, headache, seizures, dementia, cortical blindness, partial paralysis, mental retardation, motor development retardation, and brain stem abnormalities, etc. found in the brain; different levels of muscular abnormalities; myocardial hypertrophy, atrioventricular conduction abnormalities found in the heart; eyelids dropping, outer eye muscle paralysis, optic nerve degeneration, and retinopathy found in eyes; kidney tubular function abnormalities; liver function abnormalities; vomiting, diarrhea, pseudo intestinal obstruction found in the GI tract; diabetes caused by defects in the pancreas, and bone marrow malfunction. Other symptoms include deafness, short stature, injury to the peripheral nervous system, and subcutaneous lipoma, etc. In addition, a number of symptoms or diseases of aging are related to mitochondrial defects, including atherosclerosis, stroke, Parkinson's disease, Alzheimer's disease, and cancers.

Up to date, there are no cures available for mitochondria-related diseases and the most common treatment is vitamins or pyruvate. Yet, several therapies have been developed along with the expanding medical knowledge of mitochondria-related diseases, and these treatments can assess individual conditions and improve the symptoms. Theoretically, maternally inherited mitochondrial genetic defects may be prevented by transplantation using microinjection of single embryo mitochondria; however, for mutations in mitochondria caused by external factors such as oxidation stress or poor quality of the mitochondria, the present invention can provide a method that can significantly improve the efficiency of transplantation of mitochondria into a large number of cells at one time.

Mitochondria are the main energy source in eukaryotic cells; moreover, cell growth, cell differentiation, and even cell death are all regulated by mitochondria. Literatures indicate that cell fusion of stem cells and mitochondria-malfunctioned cells permit the delivery of mitochondria between cells, and consequently facilitate the repairing process of the damaged cells and restore the normal energy metabolism pathway. Therefore, positive or passive transplantation of "cell mitochondrion" has become an effective cell therapy method. Nonetheless, application of the technology remains limited due to different transplantation efficiency and cell properties. For example, only one cell can be treated using microinjection, and as a result, the efficiency of treatment is poor or the delivered mitochondria in treated cells are not transferred by fusion with other cells. Hence, no effective method that can positively deliver mitochondria into cells is available at present.

The idea of mitochondria transplantation was brought up in foreign literatures in 1998, and recent studies have also indicated that using transgenic technology to transplant mitochondria into embryos can enhance embryo development. To evaluate the effects of mitochondria transplantation on embryo development, mitochondria were separated from mouse liver cells and microinjected into the zygotes at 2PN stage collected from either young or old mice. In vitro culture of the above zygotes showed that in young mice, the percentage of the embryos developed to the blastocyst stage were significantly higher in the experimental group (37.65%) than in the control group (20.91%); however, the hatching rate was not affected (experimental group is 1.76% and control group is 1.82%). Even for the zygotes collected from older mice (about 20 weeks old), development of these embryos in the control group was also notably improved (experimental group vs. control group is 54.35% vs. 18.92% and 43.48% vs. 8.11% for embryos at morula stage and blastocyst stage, respectively). Due to ethical issues and potential risks including mitochondria heterogeneity and effects on cell activity, etc. relevant studies focused on mitochondrial transplantation in humans are not currently available. Additionally, whether the mode of transplantation is suitable for use in other cell types or other interventions are applicable requires further investigation.

Currently, mitochondrial transgenic technologies include microinjection, cell infusion, tRNA transgenic system, and peptide-mediated mitochondrial delivery system (PMD). Their respective principles, treating objects, interventional methods, and advantages/disadvantages are shown in Table 1. Among which, the peptide-mediated mitochondrial delivery system (PMD) can process a large number of cells at one time, and the number of delivered mitochondria can be regulated accordingly; moreover, the process is simple and time efficient, and no advanced techniques are required.

TABLE 1

Comparison of mitochondrial transgenic technologies.

| | Method | | | |
|---|---|---|---|---|
| | Peptide-mediated mitochondrial delivery system | Microinjection | Cell fusion | tRNA transgenic system |
| Principle | Delivers mitochondria obtained and separated from healthy cells. | Delivers mitochondria separated from healthy cells | Passive delivery via mitochondrial interaction induced by stem cell fusion | Delivers mitochondria separated from Leishmania RNA import complex (RIC) |
| Treating objects | MERRF patient-derived mitochondria fusion cell line (B2 clone) and human B143 ρ° cells treated with Ethidium Bromide to inhibit mitochondria | Mouse oocytes | Human A549 ρ° cells treated with Ethidium Bromide to inhibit mitochondria | Human MERRF patient-derived LB64 cells and mitochondrial fusion cell line KSS (FLP32.39) |
| Interventional methods | Cell penetrating peptide (Pep-1) | Microinjection | Co-culture | Liposome coating |
| Disadvantages | 1. Delivery efficiency is below 100%. 2. Average numbers of mitochondria delivered into the cells cannot be controlled accurately. | 1. One cell at a time. 2. Time consuming. 3. Requires advanced technology. | 1. Translocation of the healthy mitochondria into the damaged cells cannot be controlled. 2. Not suitable for all cell types, because cell fusion may not occur in certain cells even after co-culture. | 1. Tedious procedures. 2. Advanced technology required. 3. High cost and pre-treatment is time-consuming 4. tRNA cannot be stored ° |
| Advantages | 1. Large number of cells can be treated at one time. 2. The process of mitochondrial delivery can be regulated accordingly. 3. No advanced technology required. | Single cell transgenic rate is up to 100%. | 1. No active interventions. 2. The simplest and least expensive method. | Direct regulation of tRNA proteins, and can completely repair the defects caused by mutations in mitochondrial DNA. |

Cell penetrating peptide (Pep-1) belongs to the cell penetrating peptide families and has the sequence as shown in SEQ ID NO: 1. Pep-1 consists of 3 domains: hydrophobic domain (KETWWETWWTEW), hydrophilic domain (contains numerous lysine (K), KKKRKV), and spacer (SQP). The peptide contains both hydrophobic and hydrophilic ends, and is an amphipathic peptide. These types of peptides are usually used as drug and enzyme carriers, and they deliver their cargos by forming the particles using hydrophobic ends which cannot dissolve in water. Drugs or enzymes are then incorporated in a self-assembling reaction during the embedding process where the positive charge carried by hydrophilic domain binds to the negative charge on the cell membrane. Meanwhile, the hydrophobic domain integrates into the cell phospholipid bilayer and transports proteins into the cell. The advantage of this method is that prior chemical treatment of the target protein is not required, and the mechanism of cell entry is positive delivery, which is independent of endocytosis. Thus, the target protein will not be directly catalyzed in lysosomes, and increase cytoplasm conservation. Previous studies have also shown that Pep-1 has no cell toxicity, and its delivery will not affect ligands binding to their receptors on the cell surface.

Pep-1 peptide used in the present invention has been applied in delivery of drugs and particles; nonetheless, delivery of mitochondria using Pep-1 is a new technology developed by the present invention. In addition, by combination of the advanced mitochondria separation method, we further developed the peptide-mediated mitochondrial delivery system (PMD) which has the following advantages: the procedures are easy to follow and time efficient, one labeling process can treat numerous cells, the desired mitochondria quantity (μg) can be controlled accordingly, no cell toxicity under appropriate transplantation conditions, and transplantation efficiency can reach up to 80%. The mitochondria delivered using this system will move to the original mitochondrial sites in the cells, and will not be catalyzed in the lysosomes; hence, the therapeutic effects can last at least one week.

The present invention relates to a method using a cell penetrating peptide (Pep-1) for labeling and delivering mitochondria separated from healthy cells to replace damaged mitochondria, and can be used to treat cell mitochondrial degeneration and related diseases.

In summary, after years of painstaking research, the inventor(s) of the present invention successfully developed the novel peptide-mediated mitochondrial delivery system (PMD) and demonstrated various applications of the newly developed system.

SUMMARY OF THE INVENTION

The present invention relates to a method using a cell penetrating peptide (Pep-1) for labeling and delivering mitochondria separated from healthy cells to replace damaged mitochondria.

In one aspect, the present invention discloses a method of introduction of mitochondria into host cells, and comprises of the following features: using cell penetrating peptide that has the SEQ ID NO: 1 to label and deliver functional mitochondria and obtain peptide-mitochondria complexes; co-culture the peptide-mitochondria complexes with host cells for a specific period of time to allow introduction of the mitochondria into the host cells.

In a further embodiment of the invention, a method using cell penetrating peptide that has the SEQ ID NO: 1 to label and deliver mitochondria separated from healthy human cells, and to replace the mitochondria in damaged cells was developed. The cell penetrating peptide contains three domains including hydrophobic domain (KETWWETWW-TEW), hydrophilic domain (contains significant amount of Lysine (K), KKKRKV), and Spacer (SQP). The peptide contains both hydrophobic and hydrophilic ends, and is an amphipathic peptide. The principle of delivery is using the hydrophobic ends to gather together which cannot dissolve in water to incorporate drugs or enzymes in a self-assembling reaction during the process of embedding. The positive charge carried by the hydrophilic point will bind to the negative charge on the cell membrane and the hydrophobic end will integrate into the cell lipid bilayer simultaneously, and deliver the proteins into the cells.

In another embodiment, functional mitochondria were collected after separation from human wild type B143 fusion cell line harboring normal mitochondria, and 105 μg of mitochondria (separated from $2 \times 10^7$ cells) after quantification and labeled with Mitotracker Red was subjected to labeling with Pep-1 (SEQ ID NO: 1) for 1 h, and the resulted Pep-1/mitochondria complexes were then delivered into the host cells ($5 \times 10^4$ cells) for 2 days. Said host cells are human MERRF patient-derived B2 cells, and human B143 $\rho^\circ$ cells in which the mitochondria was inhibited by ethidium bromide, and the transplanted cells were then subjected to cellular mitochondria function assessment after one day of culture.

The advantages of the peptide-mediated mitochondrial delivery system (PMD) include simple procedures and time efficiency. One labeling process can treat a large number of cells, the number of mitochondria (μg) for delivery can be regulated accordingly, there is no cell toxicity under adequate transplantation conditions, and transplantation rate is up to 80%. The mitochondria delivered by this system will move to the original mitochondrial sites in the cell, and will not be catalyzed in lysosomes. Hence, the effects of these mitochondria delivered by this system can last for at least a week. According to present study, by using human MERRF patient-derived B2 cells and human B143 $\rho^\circ$ cells in which the mitochondria was inhibited by ethidium bromide as models, we provide evidence indicating that this PMD system can be used for treating mitochondrial degeneration and relevant diseases.

BRIEF DESCRIPTION OF THE DRAWINGS

The patent or application file contains at least one drawing executed in color. Copies of this patent or patent application publication with color drawing (s) will be provided by the Office upon request and payment of the necessary fee.

C: control group, LQ: Pep-1 group, TQ: PolyFect group.

C: control group, LQ: Pep-1 group, TQ: PolyFect group.

(# means significant difference in group C, and significant difference in group LQ).

C: control group, LQ: Pep-1 group, TQ: PolyFect group.

C: control group, LQ: Pep-1 group, TQ: PolyFect group.

FIG. 9 Assessment of mitochondrial functions. (A) Mitochondrial membrane potential assay. (B) Cell viability after glucose-starvation. *Significant differences found in control groups; +Significant differences found in experimental groups; #Significant differences found in MERRF B2 cells of the experimental groups. (C) Cell proliferation assay. *Significant differences found in control groups; +Significant differences found in experimental groups; #Significant differences found in MERRF B2 cells of the experimental groups. (D) Adenosine triphosphate (ATP) synthesis. *Significant differences found in control groups; +Significant differences found in experimental groups; #Significant differences found in MERRF B2 cells of the experimental groups. (E) Cellular lactate assay. *Significant differences found in control groups; +Significant differences found in experimental groups; #Significant differences found in MERRF B2 cells of the experimental groups.

DETAILED DESCRIPTION OF THE PREFERRED EMBODIMENT

The invention will be better understood when read in conjunction with the following detailed examples; however, the present invention is not limited to the preferred embodiments shown in the drawings.

Example 1

Detailed Description of the Peptide-Mediated Delivery System

1. Technical Process

Figure 1:
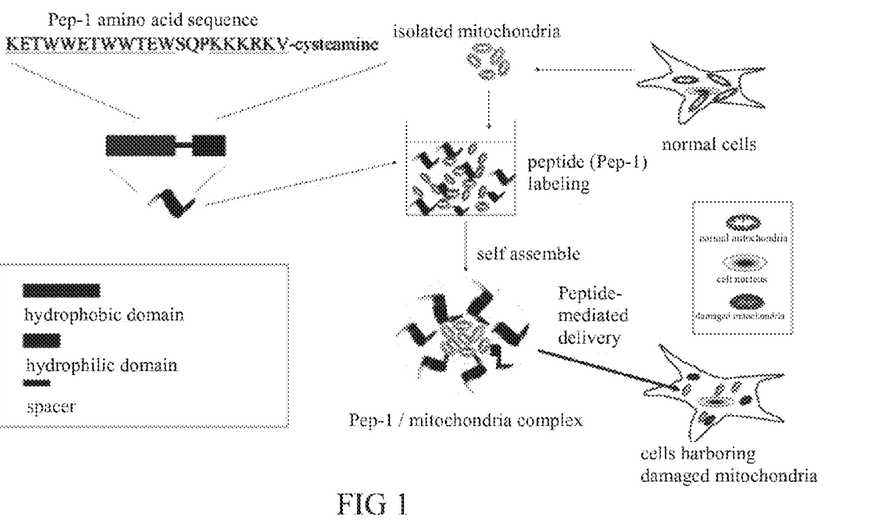
FIG. 1 The design of the peptide-mediated mitochondrial delivery system (PMD).

The present invention discloses a method using cell penetrating peptide that has the SEQ ID NO: 1 to label and deliver mitochondria separated from healthy human cells, and to replace the mitochondria in damaged cells. Said peptide-mediated delivery system is shown in FIG. 1. The cell penetrating peptide contains three domains including hydrophobic domain (KETWWETWWTEW), hydrophilic domain (contains significant amount of Lysine (K), KKKRKV), and Spacer (SQP). The peptide contains both hydrophobic and hydrophilic domains, and is an amphipathic peptide. The principle of delivery is using particles that are hydrophobic, which cannot be dissolved in water. These gather together to incorporate drugs or enzymes through a self-assembling reaction produced in the process of embedding. The positive charge carried by the hydrophilic group will bind to the negative charge on the cell membrane and the hydrophobic group will integrate into the cell lipid bilayer simultaneously, and deliver the protein into the cell. The advantages of this delivery method are that the prior chemical cross reaction of the target protein is not required, and the mechanism of delivery is by active transport which is independent of passive endocytosis; thus, the delivered proteins will not be catalyzed directly in lysosomes, and will consequently increase conservation of the cytoplasm. The literature indicates that Pep-1 has no cell toxicity, and its method of transportation will not affect ligands binding to the cell surface receptors on the host cells.

2. Experimental Results of Delivering Nanoparticles (Quantum Dots) Similar to the Size of a Mitochondrion Using the Peptide.

Figure 2:
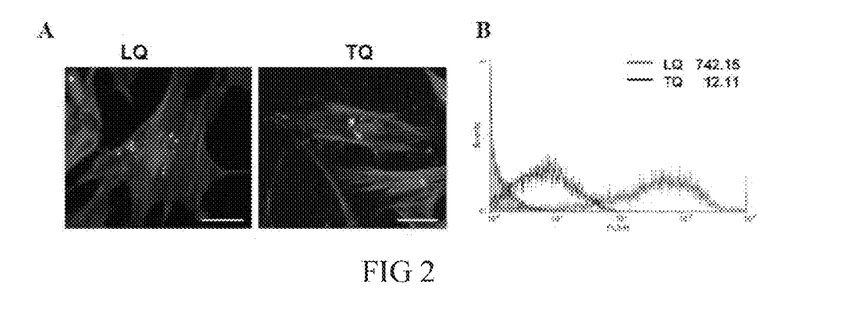
FIG. 2 The delivery efficiency of quantum dots into human adipose-derived adult stem cell (ADAS) by different methods. (A) Expression of the delivered quantum dots in cells. (B) Fluorescence intensity scattered by the particles.
Figure 3:
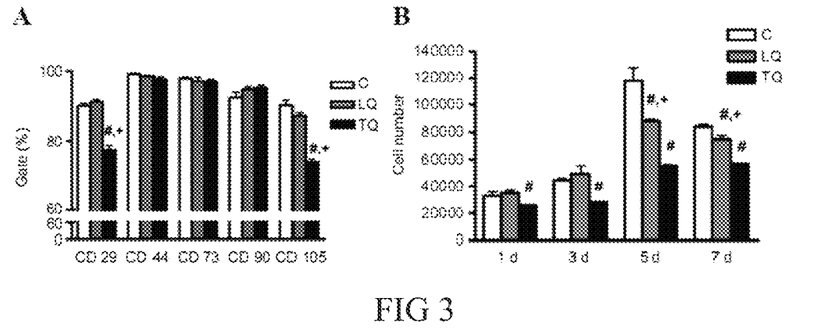
FIG. 3 Comparison of (A) target protein expression on the cell surface (one day post delivery) and (B) cell growth, of quantum dots delivered by different methods in human adipose-derived adult stem cell (ADAS).
Figure 4:
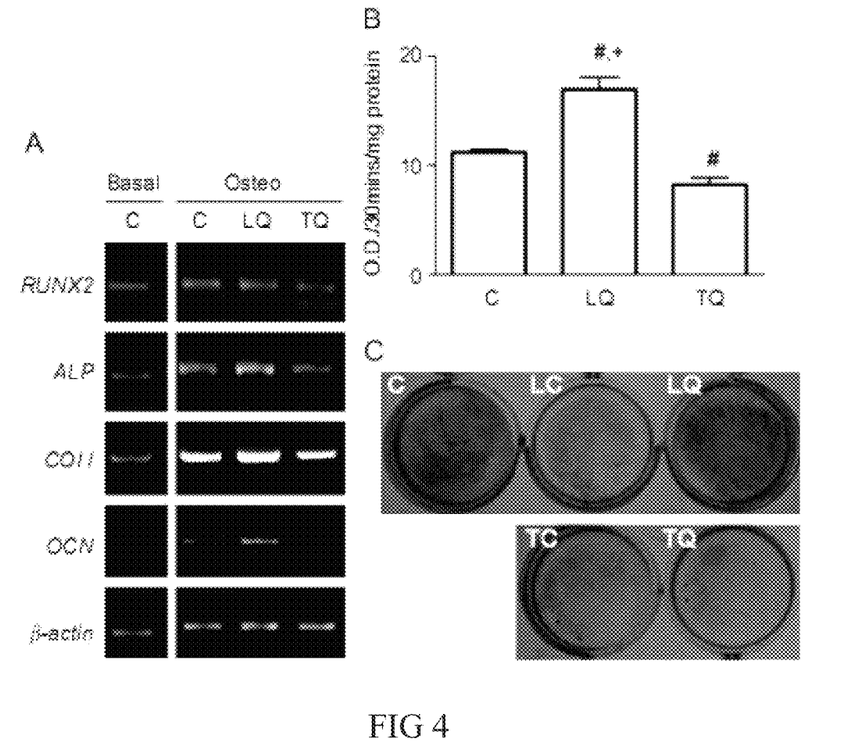
FIG. 4 Comparison of (A) bone gene expression and alkaline phosphatase activity, and (B) calcium deposition of quantum dots delivered by different methods in human adipose-derived adult stem cell (ADAS).
Figure 5:
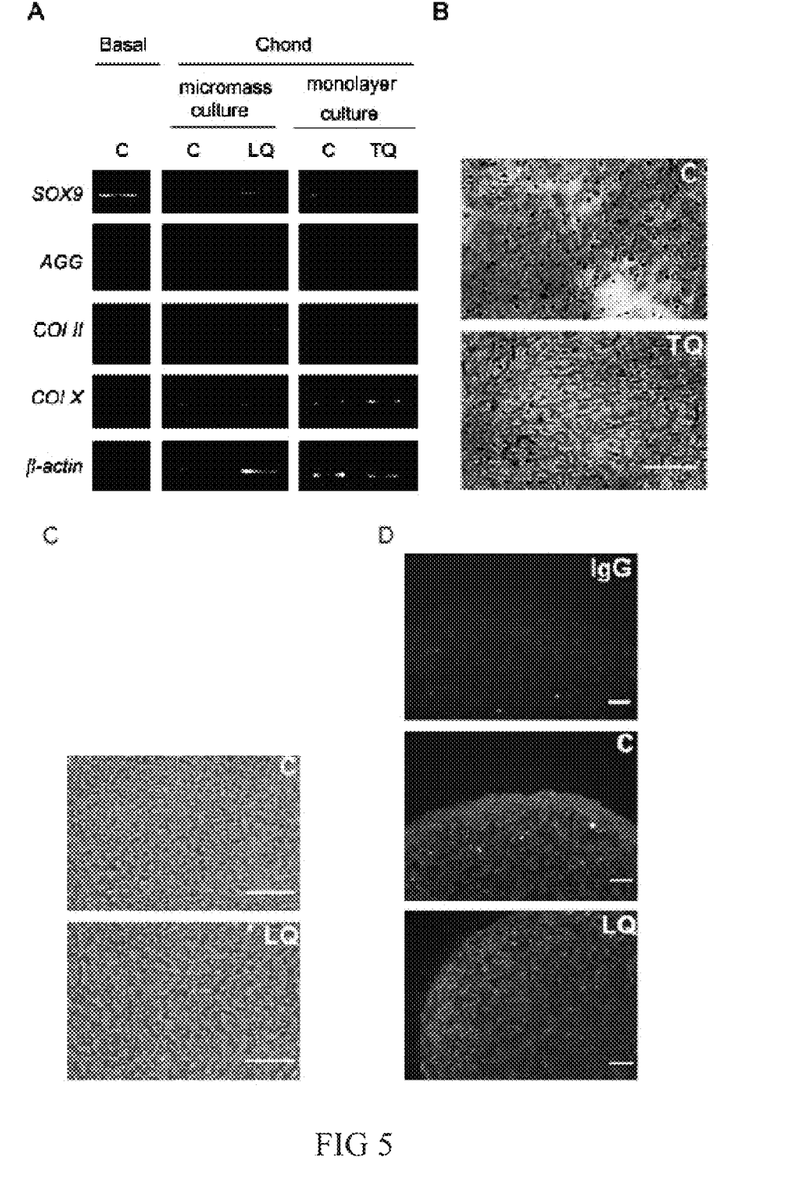
FIG. 5 Comparison of (A) cartilage gene expression, (B) (C) extracellular matrix proteoglycan expression, and (D) type II collagen expression of quantum dots delivered by different methods in human adipose-derived adult stem cell (ADAS).

The present invention also compares the methods using PolyFect reagents (TQ) which enhances the entry by endocytosis pathway and cell penetrating peptide (Pep-1), and demonstrates that delivery using Pep-1 can successfully deliver nanoparticle quantum dots (LQ). According to the fluorescence intensity, Pep-1 has higher efficiency than PolyFect reagents (as shown in FIG. 2). Meanwhile, Pep-1 will not inhibit the expression of target proteins on the cell surface (FIG. 3A) and cell growth (FIG. 3B) in human adipose-derived adult stem cell (ADAS). Furthermore, this type of delivery will not inhibit bone (FIGS. 4A and 4B) and cartilage differentiation (FIGS. 5A, 5B, and 5C) of stem cells. In contrast, delivery using PolyFect reagents (TQ) will inhibit cell differentiation and disable micromass culture, which subsequently results in immature cartilage cells.

Example 2

Assessment of the Therapeutic Effects

1. In Vitro Assessment of Peptide-Mediated Mitochondrial Delivery System (PMD)

Figure 6:
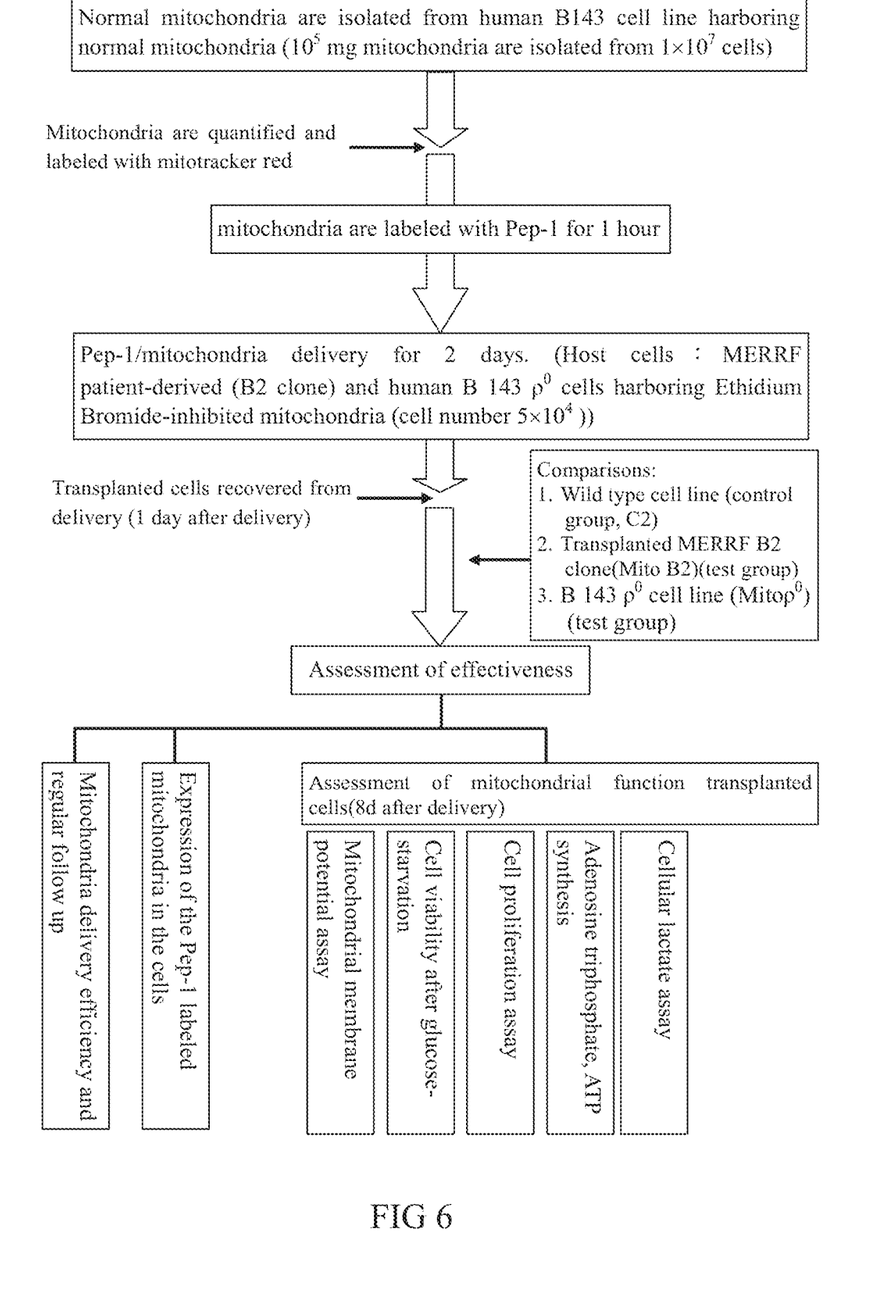
FIG. 6 Schematic diagram of in vitro assessment for Peptide-mediated mitochondrial delivery system (PMD).

Functional and normal mitochondria were separated from human B143 cell line harboring normal mitochondria, and 105 µg mitochondria (separated from $1\times10^7$ cells) was quantified and labeled with Mitotracker Red first, and then with Pep-1(SEQ ID NO: 1) for 1 hour. The resulted Pep-1/mitochondria complexes were subsequently delivered into the host cells for 2 days ($5\times10^4$ cells). Said host cells are human MERRF patient-derived B2 cells and human B143 $\rho°$ cells in which the mitochondria was inhibited by ethidium bromide, and the transplanted cells were subjected to cellular mitochondrial function assessment after one day of culture (as shown in FIG. 6).

Figure 7:
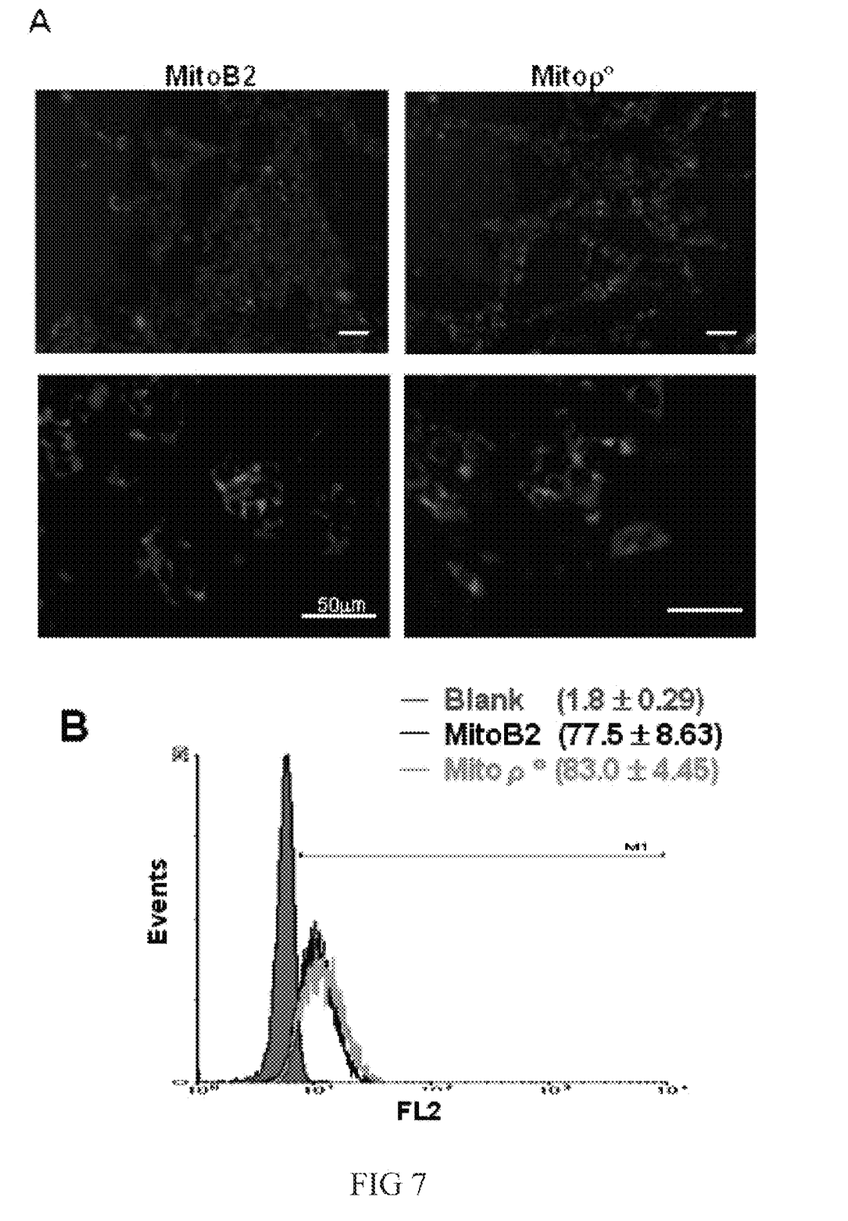
FIG. 7 (A) Pep-1 efficiently delivers mitochondria into cells (red fluorescence). (B)75.5% (MitoB2) and 83.0%)(Mitop°) of the cells express Pep-1 labeled mitochondria.

2. Confirmation and Assessment of the Therapeutic Effects (1) Mitochondrial Delivery Efficiency and Regular Follow Up Peptide Pep-1 can efficiently deliver mitochondria into cells (delivered healthy mitochondria labeled with red fluorescence) (FIG. 7A). The delivery efficiency in human MERRF patient-derived B2 clones and human B143$\rho°$cells in which the mitochondria was inhibited by ethidium bromide are 75.5% (MitoB2) and 83.0% (Mito$\rho°$), respectively (FIG. 7B).

(2) In Vitro Expression of Peptide-1 Labeled Mitochondria

Figure 8:
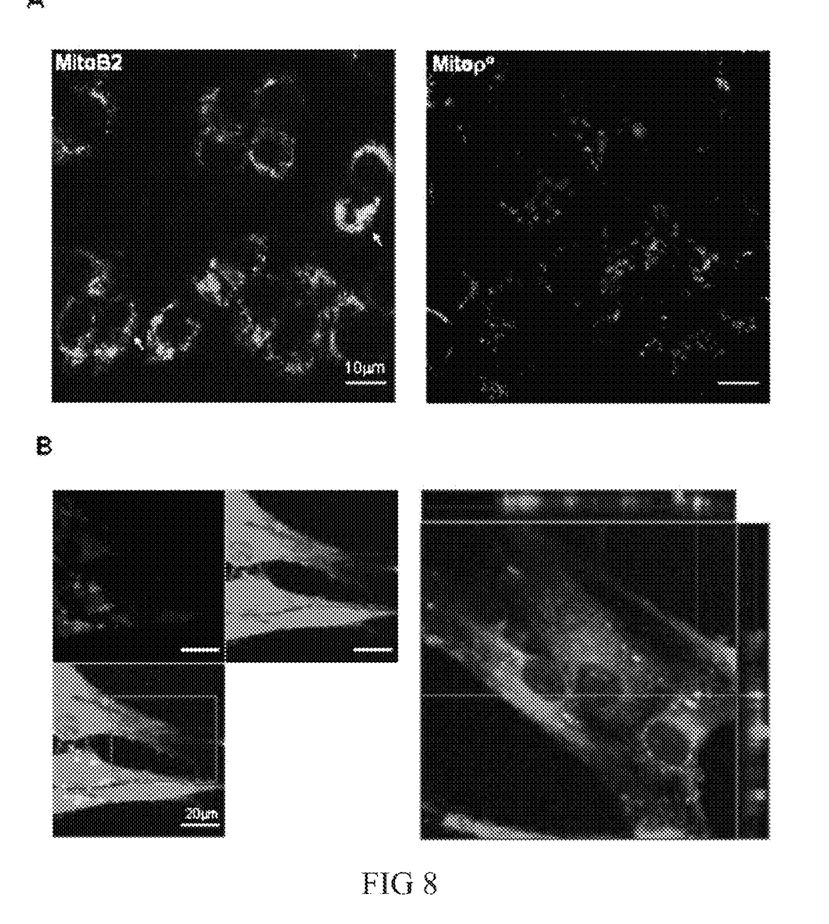
FIG. 8 (A) Expression of Pep-1 labeled mitochondria in cells. Delivered mitochondria (red fluorescence) moved to the original mitochondrial sites in the cell (green fluorescence). (B) 3D scanning results of MERRF fibroblast cells after delivery of mitochondria indicated that mitochondria can successfully enter the cells and relocate to the original mitochondrial sites in cells.

The mitochondria delivered using the present PMD system will move to the original sites of mitochondria in the cells (FIG. 8A). Using MERRF fibroblast cells that overexpress mitochondria further shows that the transplanted mitochondria can successfully enter the cells and move to the original mitochondria sites in the cells (FIG. 8B).

(3) Evaluation of the Repair Function of Peptide-1 Targeted Mitochondria

Figure 9A:
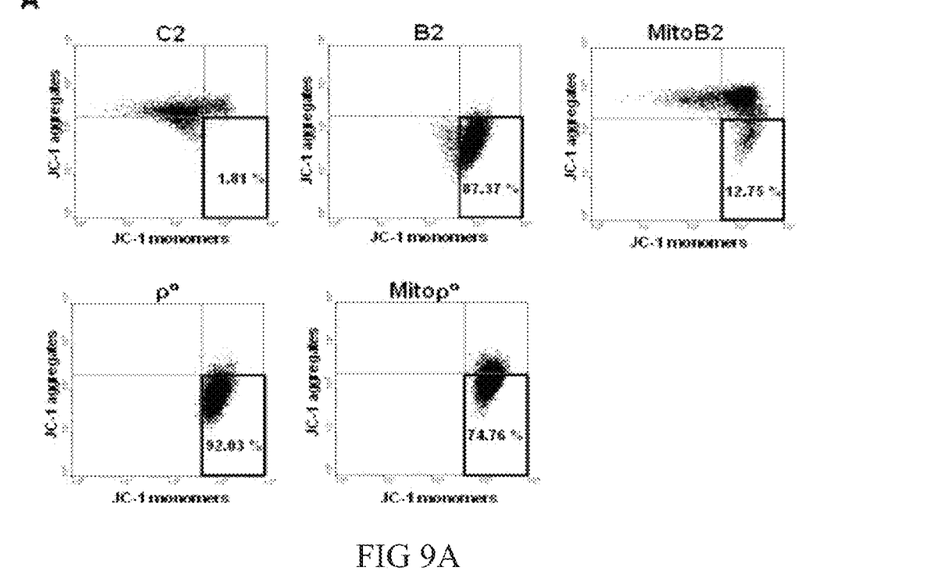
Figure 9B:
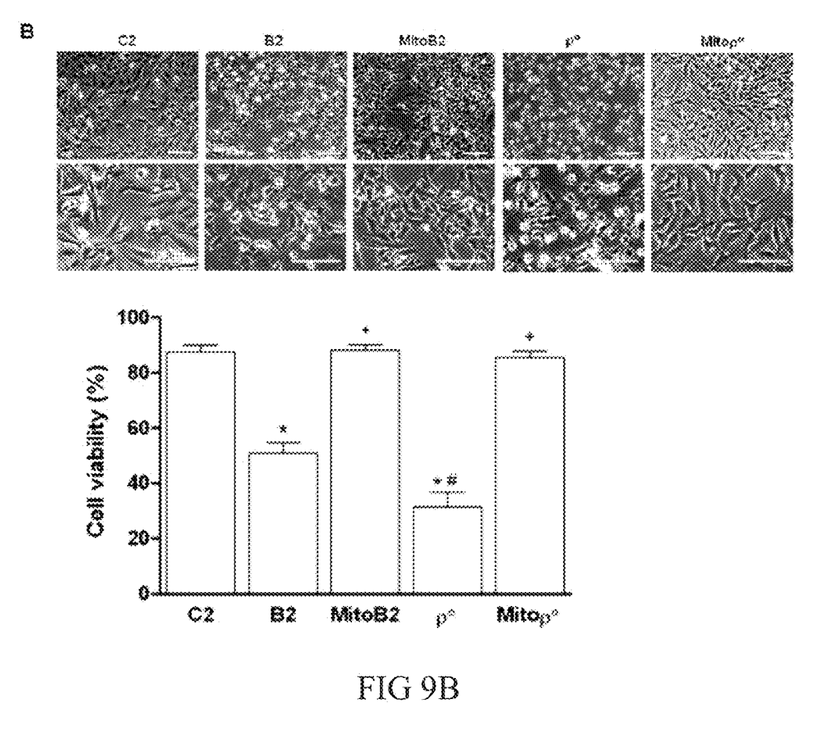
Figure 9C:
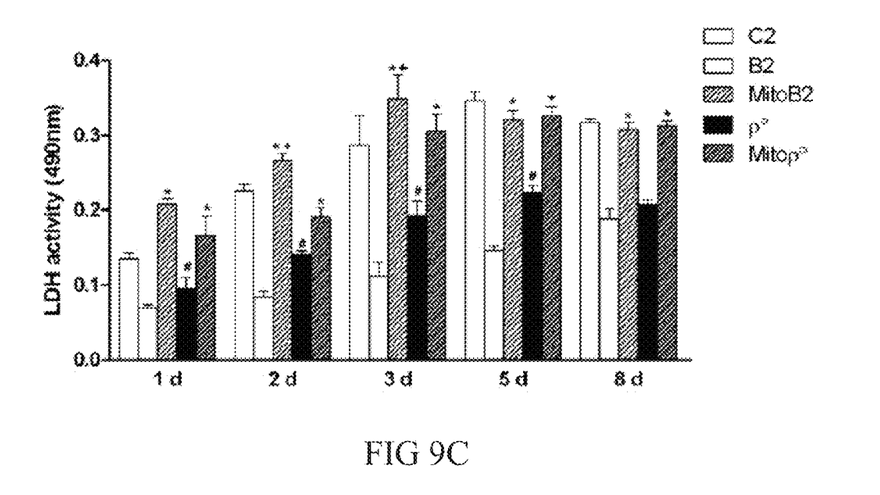
Figure 9D:
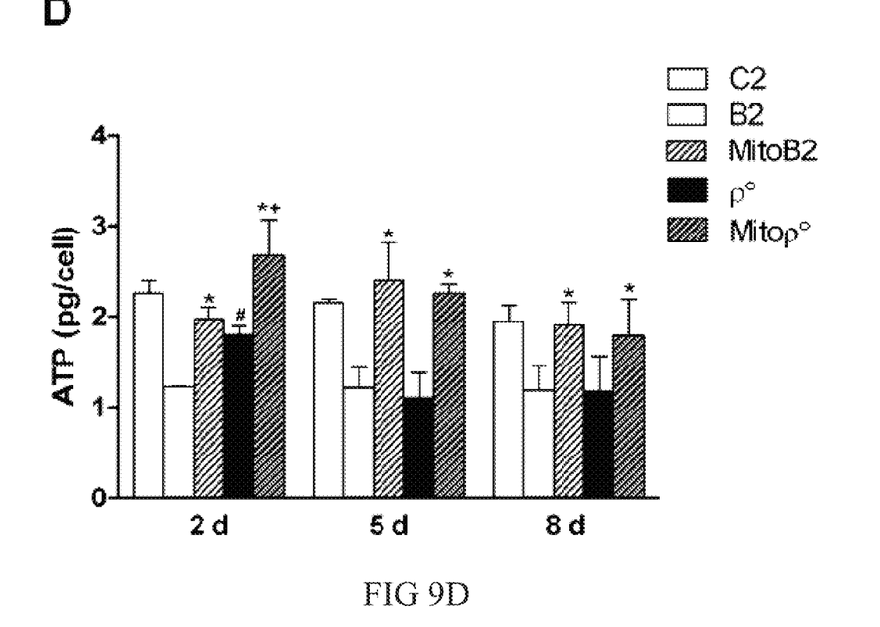
Figure 9E:
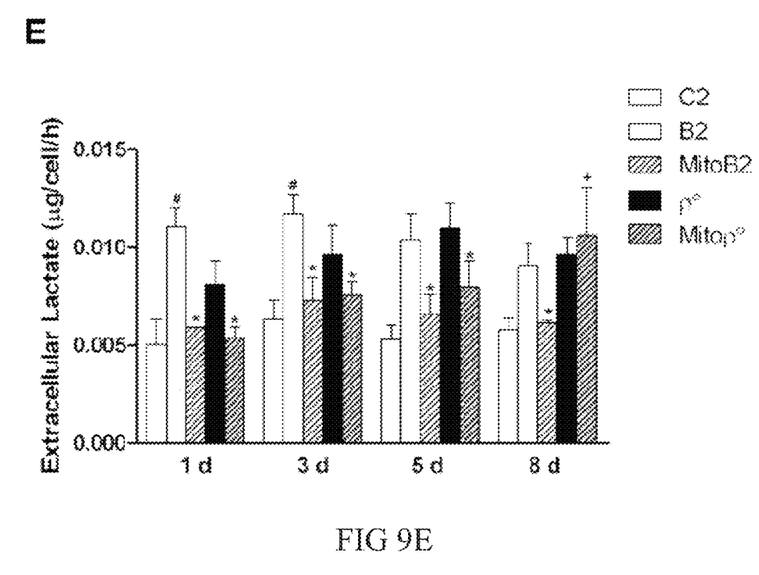

Peptide-mediated mitochondrial delivery system (PMD) has no cell toxicity, and can be used to treat cell mitochondrial malfunction caused by mutations in mitochondrial DNA, including recovering mitochondrial membrane potential (reduced JC1 monomers fluorescence expression) (FIG. 9A), prolonging cell survival in low-sugar culture condition (FIG. 9C), recovering production of cell energy (FIG. 9D), and reducing lactate produced in anaerobic metabolism process (FIG. 9E). The therapeutic effects of PMD last at least one week.

(4) According to the results, the system is suitable for use in various types of cells that have functional mitochondria defects found in myoclonic epilepsy with ragged-red fibers (MERRF) syndrome which includes MERRF lymphocytes (MERRF LCL), and MERRF fibroblasts.

Figure 10A:
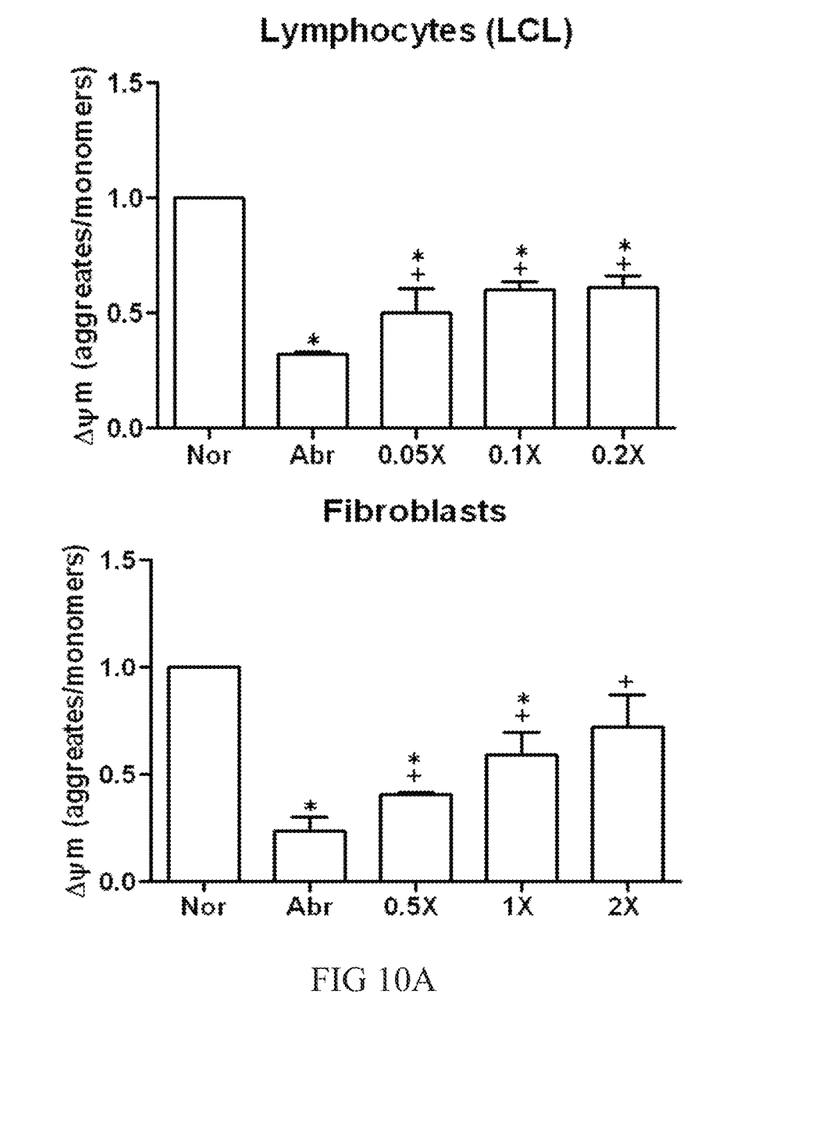
FIG. 10 Assessment of mitochondrial function, therapeutic effects, delivered at different concentrations in human MERRF LCL cells and MERRF fibroblasts. (A) Mitochondrial membrane potential assay. (B) Reactive oxygen species (ROS) stress test. *Significant differences found in control groups; +Significant differences found in experimental groups Nor: normal cells, Abr: abnormal cells.
Figure 10B:
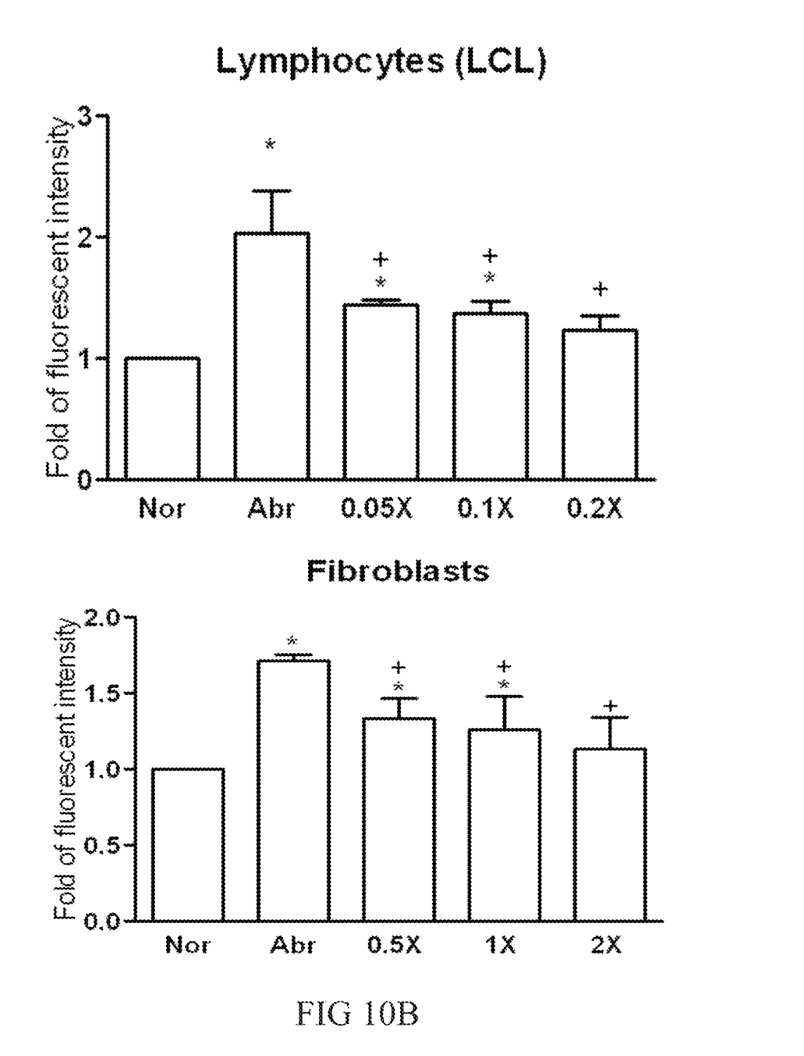

The peptide-mediated mitochondrial delivery system (PMD) was shown to restore the function of damaged mitochondria of MERRF (Myoclonic Epilepsy with Ragged Red Fibers) patients-derived lymphocytes (MERRF LCL), and fibroblasts (MERRF fibroblasts). At appropriate mitochondria concentration, MERRF LCL (compared with the mitochondria concentrations prior to transportation: 0.05×, 0.1×, 0.2×) and MERRF fibroblasts (compared with the mitochondria concentrations prior to transportation: 0.05×, 0.1×, 0.2×), mitochondria malfunction caused by gene mutations in mitochondria are notably reduced, including increased mitochondrial potential (increased fluorescence expression of JC1 aggregates)(FIG. 10A), and reduced production of intracellular reactive oxygen species (ROS) (FIG. 10B).

The peptide-mediated mitochondrial delivery system (PMD) described in the present invention has the following advantages when compared with other well-known systems used for delivering mitochondria:
 1. No cell toxicity effects on the host cells.
 2. Efficient delivery of nanoparticles into stem cells and no effects on stem cell differentiation.
 3. The delivered particles will not activate cell metabolism pathways, and can be catalyzed.

Taken together, the peptide-mediated mitochondrial delivery system is a feasible technology and has been proved in the examples mentioned above. Though Pep-1 has been used in delivery of drugs and particles, delivery of mitochondria using Pep-1 is a new technology developed by the present invention. In addition, the present system also includes an advanced mitochondria separation method. The procedures of the PMD system are easy to follow and very efficient. One labeling process can treat numerous cells, the desired mitochondria quantity (μg) can be controlled accordingly, there is no cell toxicity under appropriate transplantation conditions, and most importantly, transplantation efficiency is up to 80%. The mitochondria delivered using this system will not only move to the original mitochondrial sites in the cell, but will not be catalyzed in the lysosomes; hence, the therapeutic effects can last at least one week. According to the results, using MERRF B2 cell line derived from patients with MERRF syndrome, and human B143 ρ° cell line in which mitochondria were inhibited by ethidium bromide as models, we demonstrated that the present system can be used for treating cell mitochondrial degeneration and related diseases. Furthermore, this study further confirmed the feasibility of the present system in that with adequate mitochondria transplantation numbers, therapeutic effects are outstanding by using different cells derived from MERRF patients, including MERRF LCL and MERRF fibroblasts.

The peptides used in the invention are not toxic; however, preliminary evaluation to determine the adequate number of mitochondria for delivery for optimal results is required. The effective number of delivered mitochondria in different types of cells may vary accordingly. For example, as shown in the present invention, after calculation of the ratios of the peptides, 105 μg of mitochondria is effective in treating 50,000 mutant mitochondria in B2 cybrids cells derived from MERRF patients. Excess delivery of mitochondria may result in cell stress and induce cell growth arrest.

The foregoing descriptions are detailed examples to better elucidate the present invention; however, the applications of the present invention is not limited to the description provided here, and all related modifications/applications should be included in the present invention.

In summary, the present invention meet the requirements of Article 33 (2) PCT and 33(3) PCT, and therefore, is considered novel and inventive.

What is claimed is:

1. A method for introducing a mitochondria into host cells, the method comprising: comprising labeling the normal mitochondria with a peptide that has the sequence as shown in SEQ ID NO:1, and the labeled mitochondria was subsequently co-cultured with host cells for a specific period of time to allow delivery of the labeled mitochondria into the host cells; wherein said host cells are selected from a group consisting of human MERRF patient-derived B2 cells, MERRF LCL, MERRF fibroblasts, and human B143 ρ° cells.

2. The method according to claim 1, wherein the normal mitochondria are separated from normal cells.

3. The method according to claim 2, wherein the normal and functional mitochondria are separated from normal human cells.

4. The method according to claim 1, wherein the peptide is an amphipathic peptide which contains both hydrophilic and hydrophobic domain.

5. The method according to claim 4, wherein the peptide contains hydrophobic domain, hydrophilic domain, and spacers.

6. The method according to claim 1, wherein the normal mitochondria are labeled with the peptide that has the SEQ ID NO: 1 for less than 3 hours.

7. The method according to claim 1, wherein the host cells are selected from mitochondria-dysfunction host tissues or cells.

8. The method according to claim 1, wherein the time of interaction (co-culture) for labeled mitochondria and the host cells lasts less than 3 days.

9. The method according to claim 1, wherein the ratio of labeled mitochondria to host cells is 1 μg of mitochondria to up to 500 host cells.

10. A composition for introducing a mitochondria in to host cells comprising a peptide that has SEQ ID NO:1, a normal and functional mitochondria, and a pharmaceutically acceptable excipient.

11. The composition according to claim 10, wherein the normal mitochondria in the composition are obtained from normal cells after separation.

12. The composition according to claim 11, wherein the normal and functional mitochondria in the composition are obtained from normal human cells after separation.

13. The composition according to claim 10, wherein the peptide is an amphipathic peptide and contains both hydrophilic and hydrophobic groups.

14. The composition according to claim 13, wherein the peptide contains hydrophobic domain, hydrophilic domain, and spacers.

15. The composition according to claim 10, wherein the excipients are diluents, fillers, binders, disintegrating agents, or lubricants.

* * * * *